United States Patent
Lin et al.

(10) Patent No.: US 12,188,077 B2
(45) Date of Patent: *Jan. 7, 2025

(54) MULTIPLEXED IMMUNOSIGNAL AMPLIFICATION USING HYBRIDIZATION CHAIN REACTION-BASED METHOD

(71) Applicant: GenAns Biotechnology Co., Ltd, Beijing (CN)

(72) Inventors: Rui Lin, Beijing (CN); Minmin Luo, Beijing (CN)

(73) Assignee: GenAns Biotechnology Co., Ltd, Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/045,811

(22) Filed: Oct. 11, 2022

(65) Prior Publication Data

US 2023/0220445 A1 Jul. 13, 2023

Related U.S. Application Data

(63) Continuation of application No. 15/733,419, filed as application No. PCT/CN2018/074364 on Jan. 26, 2018, now abandoned.

(51) Int. Cl.
*C12Q 1/6804* (2018.01)
*C12Q 1/6832* (2018.01)
*G01N 33/58* (2006.01)
*G01N 33/68* (2006.01)

(52) U.S. Cl.
CPC ......... *C12Q 1/6804* (2013.01); *C12Q 1/6832* (2013.01); *G01N 33/582* (2013.01); *G01N 33/6875* (2013.01); *C12Q 2600/16* (2013.01)

(58) Field of Classification Search
CPC ............ C12Q 1/6804; C12Q 2563/131; G01N 33/582
See application file for complete search history.

(56) References Cited

U.S. PATENT DOCUMENTS

2006/0228733 A1* 10/2006 Pierce ..................... C12Q 1/682
536/25.32
2018/0164308 A1 6/2018 Walter et al.
2020/0377926 A1* 12/2020 Lin ....................... C12Q 1/6818

FOREIGN PATENT DOCUMENTS

| CN | 106222276 A | 12/2016 |
| CN | 106771174 A | 5/2017 |
| WO | 2018017604 A1 | 1/2018 |

OTHER PUBLICATIONS

Zhang et al., "DNA-Based Hybridization Chain Reaction for Amplified Bioelectronic Signal and Ultrasensitive Detection of Proteins", Analytical Chemistry, vol. 84, pp. 5392-5399 (Year: 2012).*
Zhou, Hong et al.; "Universal immuno-PCR for ultra-sensitive target protein detection"; Nucleic Acids Research; vol. 21, No. 25; Nov. 1993; pp. 6038-6039.
Kolberg et al.; "SNAP-Tag Technology: A General Introduction"; Current Pharmaceutical Design, vol. 19; Year: 2013; pp. 5409-5413.
Choi, Jonghoon et al., "Immuno-Hybridization Chain Reaction for Enhancing Detection of Individual Cytokine-Secreting Human Peripheral Mononuclear Cells," Analytical Chemistry, vol. 83, Year: 2011; pp. 6890-6895.
Zhang, Bing et al., "DNA-Based Hybridization Chain Reaction for Amplified Bioelectronic Signal and Ultrasensitive Detection of Proteins," Analytical Chemistry, vol. 84, Year: 2012; pp. 5392-5399.
Ge Jia et al., "A novel graphene oxide based fluorescent nanosensing strategy with hybridization chain reaction signal amplification for highly sensitive biothiol detection," ChemCommun, vol. 50, Year 2014; pp. 11879-11882.
Xu, Wentao et al., "A rapid and visual aptasensor for Lipopolysaccharide detection based on the bulb-like triplex turn-on switch coupled with HCR-HRP nanostructures," Biosensors and Bioelectronics, vol. 89, Oct. 5, 2016; pp. 795-801.
Gong, Haibiao et al., "Simple Method to Prepare Oligonucleotide-Conjugated Antibodies and Its Application in Multiplex Protein Detection in Single Cells," Bioconjugate Chemistry, vol. 27, Year: 2016; pp. 217-225.
Choi, Harry M. T. et al., "Next-generation in Situ hybridization chain reaction: higher gain, lower cost, greater durability", ACS Nano., May 27, 2014, vol. 8, No. 5, pp. 4284-4294.
Koos et al., "Proximity-dependent initiation of hybridization chain reaction", Nature Communication, No. 6:7294; Jun. 12, 2015, 10 sheets.
Ssylwestrak, Emily Lauren et al., "Multiplexed intact-tissue transcriptional analysis at cellular resolution", Cell. Feb. 11, 2016, vol. 164, No. 4, pp. 792-804.
Han et al., "Microfluidic Chips for Immunoassays", Annual Review of Analytical Chemistry, 2013, pp. 119-141.
Bobrow et al., "Catalyzed reporter deposition, a novel method of signal amplification. Application to immunoassays", J. ofImmunological Methods, 1989, vol. 125, pp. 279-285.
Stack et al., "Multiplexed immunohistochemistry, imaging, and quantitation: A review, with an assessment ofTyramide signal amplification, multispectral imaging and multiplex analysis", Methods, 2014, vol. 70, pp. 46-58.
Carvajal-Hausdorf et al., "Quantitative measurement of cancer tissue biomarkers in the lab and in the clinic", Laboratory Investigation, 2015, vol. 95, pp. 385-396.
Shah et al., "Single-molecule RNA detection at depth by hybridization chain reaction and tissue hydrogel embedding and clearing", Development, 2016, vol. 143, pp. 2862-2867.

* cited by examiner

*Primary Examiner* — Young J Kim
(74) *Attorney, Agent, or Firm* — NKL Law; Allen Xue

(57) ABSTRACT

The invention provides a method for optimizing isHCR for multiplexed labeling, which combines binder-biomolecule interactions with hybridization Chain Reaction (HCR).

6 Claims, 2 Drawing Sheets

Specification includes a Sequence Listing.

MULTIPLEXED IMMUNOSIGNAL AMPLIFICATION USING HYBRIDIZATION CHAIN REACTION-BASED METHOD

CROSS-REFERENCE TO RELATED APPLICATIONS

This application is a continuation of U.S. patent application Ser. No. 15/733,419, filed Jul. 23, 2020, which is a U.S. national stage entry of PCT international application no. PCT/CN2018/074364, filed Jan. 26, 2018, the content of each is incorporated herein by reference in its entirety

INCORPORATION OF SEQUENCE LISTING

This application contains a sequence listing submitted in Computer Readable Form (CRF). The CFR file containing the sequence listing entitled "SequenctListing.xml", which was created on Oct. 11, 2022, and is 13,655 bytes in size. The information in the sequence listing is incorporated herein by reference in its entirety.

BACKGROUND

Owing to their ease of use, speed, and cost effectiveness, antibody-based immunoassays remain the most popular methods for detecting and identifying the location of proteins and other biomolecules in biological samples. These methods use a primary antibody that binds selectively to a target molecule (antigen), and this antibody-antigen interaction can be visualized via a conjugated reporter or a labeled secondary antibody that can recognize and react with the primary antibody-epitope complex (Han, K. N., Li, C. A. & Seong, G. H. *Annu. Rev. Anal. Chem.* 6, 119-141 (2013)). A major limitation in the use of immunoassays is that the low abundance of a given target molecule in a sample often necessitates signal amplification before detection is possible. Amplification can be achieved using conjugated enzymes such as horseradish peroxidase (HRP) and alkaline phosphatase, which catalyze the deposition of chromogenic substrates on target complexes (Bobrow, M. N., Harris, T. D., Shaughnessy, K. J. & Litt, G. J. *J. Immunol. Methods* 125, 279-285 (1989)). Fluorogenic substrates, especially those based on HRP-tyramide reaction chemistries, have been developed to support high-resolution fluorescence microscopy (Stack, E. C., Wang, C., Roman, K. A. & Hoyt, C. C. *Methods* 70, 46-58 (2014)). Although very useful and widely-employed, current amplification methods have several drawbacks: they often generate high background, they can reduce spatial resolution due to dye diffusion, they are difficult to use for the simultaneous detection of multiple amplified signals (Carvajal-Hausdorf, D. E., Schalper, K. A., Neumeister, V. M. & Rimm, D. L. *Lab. Invest.* 95, 385-396 (2015)), and they are unsuitable for use with large-volume samples in several powerful new tissue expansion and clearing techniques.

In this invention, we find that an enzyme-free amplification approach could overcome many of these limitations. In particular, hybridization chain reaction (HCR) technology is adapted to amplify immunosignals. HCR, which is based on recognition and hybridization events that occur between sets of DNA hairpin oligomers that self-assemble into polymers, has to date been used primarily for the amplification of mRNA signals from in situ hybridization samples (Choi, H. M. T., Beck, V. A. & Pierce, N. A. *ACS Nano* 8, 4284-4294 (2014); Shah, S. et al. *Development* 143, 2862-2867 (2016)) and more recently for the detection of protein-protein interactions (Koos, B. et al. *Nat. Commun.* 6, 7294 (2015)), and more recently for the detection of protein-protein interactions (Koos, B. et al. *Nat. Commun.* 6, 7294 (2015)). In a typical usage case, nucleic acid probes complementary to the target mRNA molecule are used as 'initiator' oligos. Starting from the initiator oligos, a series of polymerization reactions are used to add fluorophore-labeled nucleic acid 'amplifier' oligos to the target mRNA-initiator complex; the fluorophores are then visualized.

SUMMARY OF THE INVENTION

The invention provides a method for optimizing isHCR for multiplexed labeling, which combines binder-biomolecule interactions with hybridization Chain Reaction (HCR), wherein the initiators used in the isHCR are modified directed to multiple targets respectively to allow simultaneous isHCR amplification of multiple targets. The invention also provides a kit for performing the method for optimizing isHCR for multiplexed labeling.

In the first aspect, the invention provides a method for detecting multiple target biomolecules, which combines binder-biomolecule interactions with hybridization Chain Reaction (HCR), wherein orthogonal binders for conjugating orthogonal initiators and targeting multiple target biomolecules, and orthogonal initiators directed to orthogonal binders respectively are used in HCR to allow HCR amplification of multiple target biomolecules.

In the second aspect, the invention provides a kit for detecting multiple target biomolecules, which comprises (1) orthogonal binders; (2) orthogonal HCR initiators; and (3) orthogonal pairs of HCR amplifiers' wherein each of HCR initiators has a region for hybridizing with a HCR amplifier, and a region for conjugating a binder, and the orthogonal binders target multiple target biomolecules respectively to allow HCR amplification directed to multiple target biomolecules.

The binder can be an antibody, a fragment of an antibody, or a genetically-engineered protein tag. If the orthogonal binders are orthogonal antibodies, the antibodies may be biotinylated antibodies, and the orthogonal HCR initiators may be biotinylated initiators for conjugating the vacant binding sites of streptavidin, which is capable of conjugating to the biotinylated antibodies in order to sequentially amplify multiple target biomolecules.

Preferably, the orthogonal HCR initiators may be directly conjugated to the orthogonal binders using chemical linkers so as to simplify the multiplexed labeling procedure. The chemical linkers can be amine-reactive linkers, thiol-reactive linkers or click chemistry linkers. The amine-reactive linkers can be linkers containing succinimidyl ester group. The click chemistry linkers can be linkers containing click chemistry functional groups, such as NHS Azide linkes, NHS-DBCO linkers, maleimide-azide linkers, or maleimide-DBCO linkers. For example, the orthogonal HCR initiators can be conjugated directly onto the binders via SMCC or NHS-Azide linkers. This direct conjugation allows simultaneous HCR amplification directed to multiple target biomolecules.

Preferably, the antibody may be a secondary antibody that reacts with a primary antibody specific to an analyte, the secondary antibody is a IgG or a Nanobody, and the primary antibody is a IgG, a Nanobody or a scFv.

In the situation that the binder is a genetically-engineered protein tag, the orthogonal HCR initiators can be conjugated to tag binding partners, which are capable of binding tags labeling different target biomolecules. The biomolecules can be biomolecules, such as proteins, small signaling molecules, neurotransmitters, etc., in the cells. The tag has a chemical group nonreactive toward a biomolecule, said chemical group is selected from an amine moiety, a carboxyl moiety, a thiol moiety and a glycosylated modification moiety. The HCR initiators are conjugated to tag binding partners, and subsequently are used for HCR amplification to detect tags. The persons skilled in the art may easily choose the tags and tag binding partners as desired.

The tags may be orthogonal tags targeting different cellular locations and being expressed in cultured cells. In this situation, the HCR initiators may be conjugated to tag binding partners (for example, SpyCatcher, SnoopCatcher, benzylguanine (BG), and scFv), and subsequently are used to detect the subcellular localization of the genetically-encoded tags (SpyTag, SnoopTag, SNAP-tag, and GCN4-tag). CLIP-tag and Halo-tag, two chemical tags that are orthogonal to the SNAP-tag technology, could also be adopted for HCR in a fashion similar to SNAP-tag. Recently, novel mini-protein binders that target small ligands were developed using de novo protein design. These new ligand-binder pairs, such as digoxigenin/DIG10.3 also can be used with HCR.

Therefore, these extensions of HCR concept beyond biotin-streptavidin interactions and beyond primary and secondary antibodies demonstrate that HCR can be implemented in a highly multiplexed fashion. These direct conjugation strategies will also reduce the size of isHCR amplification complexes.

The isHCR may be multi-round isHCR, in which an amplifier or a pair of amplifiers are modified to access branched multiple-round amplification in order to branch and grow the HCR polymers.

The HCR initiators can be hybridized with any of several types of self-assembling DNA HCR amplifiers, including a fluorophore-labeled amplifier oligo that can be used for visualization of the original target signal.

The HCR amplifiers (H1 and H2) used in the present multi-round isHCR can be terminally modified or internally modified with chemical groups and/or fluorescent dyes, which allows initiating further rounds of amplification. In this situation, the amplifiers (H1 and H2) can be terminally modified or internally modified with biotin, digoxigenin, acrydite, amine, succinimidyl ester, thiol, azide, TCO, Tetrazine, Alkyne, and/or DBCO. Fluorescent dye, such as FITC, Cyanine dyes, Alexa Fluors, Dylight fluors, Atto dyes or Janelia Fluor dyes, can be also tagged to the amplifiers together with biotin, digoxigenin, acrydite, amine, succinimidyl ester, thiol, azide, TCO, Tetrazine, Alkyne, and/or DBCO. For example, amplifiers can be labeled with bitoin groups. Once these DNA-biotin amplifiers have self-assembled and joined the growing isHCR polymer, their biotins can be reacted with newly-added streptavidins (and hence can be reacted with more HCR initiators, etc.), thereby initiating further rounds of polymer elaboration. A pair of signal molecule-modified amplifiers (e.g., a pair of fluorophore-tagged amplifiers) can be added to the final round of isHCR" for visualization.

Preferably, the amplifiers are modified at internal positions, which are more accessible to the binding partners, such as streptavidins, which serve as anchors for each successive round of branching in multi-round isHCR (isHCR").

The present method may also comprise using grapheme oxide (GO) to absorb unassembled HCR amplifiers. If the amplifiers are terminally modified and/or internally modified with fluorescent dye, grapheme oxide (GO) may also quench the fluorescence. Therefore, the kit of the present invention may also comprise grapheme oxide. Graphene Oxide in the present invention has a particle size of <500 nm. Crucially, in addition to abolishing the fluorescence of HCR amplifiers, the addition of HCR initiators along with HCR amplifiers and GO resulted in substantial recovery of fluorescence, likely because the initiators triggered the formation of double-strand-nicked polymers of HCR amplifiers, thereby protecting them from the adsorption activity of GO. That is, GO can be used to suppress background levels, further enhancing the performance of isHCR.

The addition of GO reduced the background but did not diminish the signal intensity, resulting in an improved signal-to-noise ratio as compared to isHCR amplification without GO. Surprisingly, further analysis using antibody serial dilution experiments showed that isHCR with GO significantly increased signal intensity as compared to a standard IHC staining method, achieving a greater than 80× amplification factor when the primary antibody was highly diluted.

The invention encompasses all combination of the particular embodiments recited herein.

DESCRIPTION OF PARTICULAR EMBODIMENTS OF THE INVENTION

Figure 1:
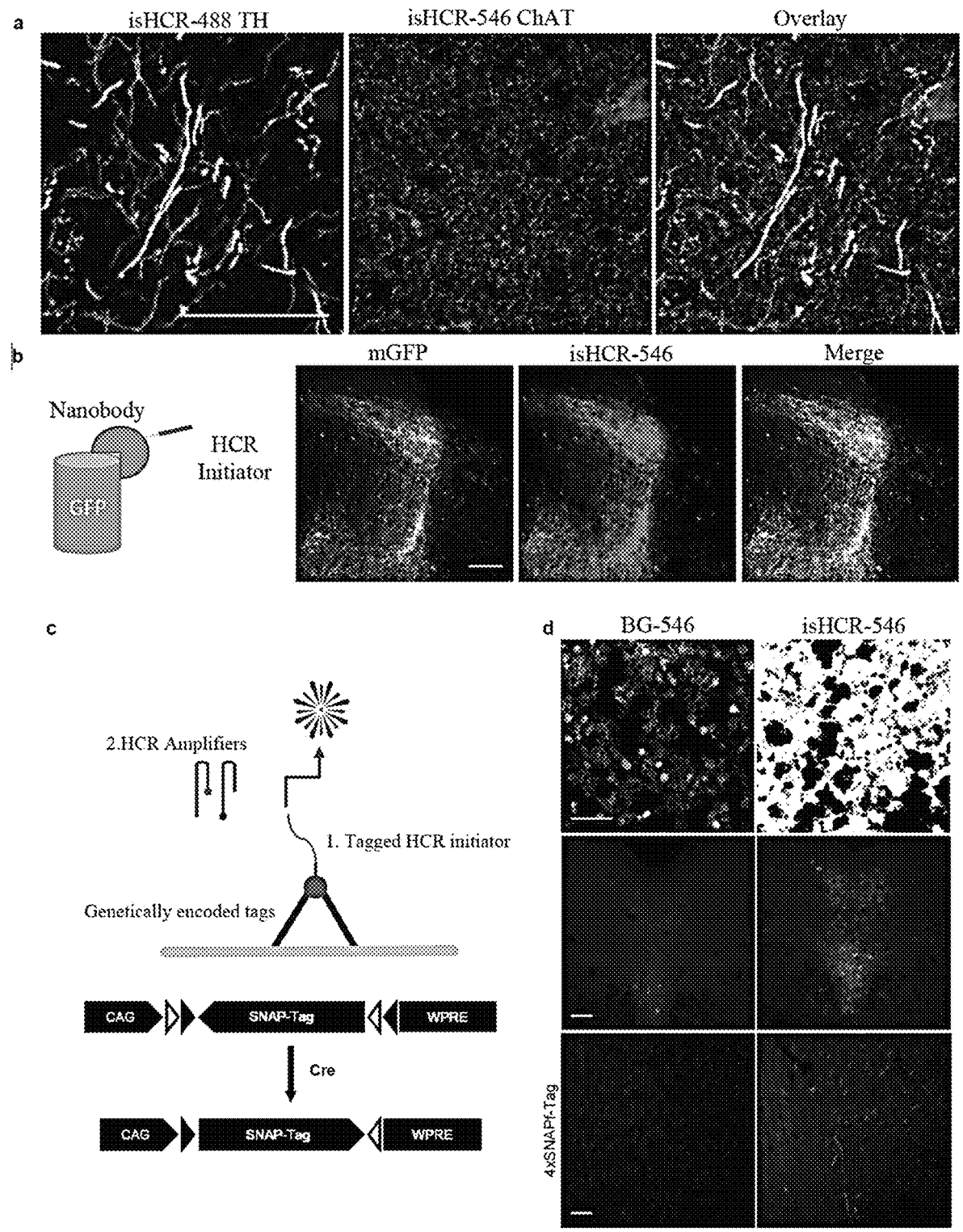
FIG. 1. Multiplexed labeling using isHCR.

In the first embodiment, we established the use of two biotinylated secondary antibodies in combination with two orthogonal DNA HCR initiators, which allows isHCR to sequentially amplify two targets in the same brain section sample (FIG. 1a).

In the second embodiment, we directly conjugated DNA HCR initiators to secondary antibodies via SMCC or NHS-Azide linkers (FIG. 2a). This modification allows simultaneous isHCR amplification of multiple targets. We successfully performed multiplexed isHCR amplification using initiator-labeled secondary antibodies in western blotting (FIG. 2b), immunostaining of cultured cells (FIG. 2c), and immunostaining of brain sections (FIG. 2d).

In the third embodiment, with the goal of expanding the modularity of the isHCR platform yet further, we tested whether a variety of genetically-engineered protein tags could be added to target proteins in cells to enable the direct binding of targets to HCR initiators. Three orthogonal tags targeting different cellular locations (SpyTag for cell nuclei, SNAP-tag for mitochondria, and smFP_GCN4 for cell membranes) were expressed in cultured cells. DNA HCR initiators were conjugated to tag binding partners (SpyCatcher, benzylguanine (BG), and scFv), and these were subsequently used for isHCR amplification to detect the subcellular localization of the genetically-encoded tags (FIG. 2e). Strong and correctly localized signals were observed for each tag.

In the fourth embodiment, we next expressed membrane-bound GFP in brains and confirmed that HCR initiators conjugated to GFP nanobodies22 could bind directly to GFP, allowing for subsequent polymerization and detection of HCR amplifiers in brain sections (FIG. 1b).

In the fifth embodiment, we expressed the SNAP-tag in mouse brains and applied BG-functionalized HCR initiators for direct detection and amplification (FIG. 1c, d). We noted that labeling neurons with a monomeric SNAP-tag only generated weak signals at soma (FIG. 1d middle panel). We therefore employed a tandem SNAP-tag to enhance the labeling intensity. This optimization greatly increased the signal intensity and allowed for the detection of distal axons of labeled neurons (FIG. 1d bottom panel).

HCR is the abbreviation of Hybridization Chain Reaction. When a single-stranded DNA initiator is added to a reaction system, it opens a hairpin of one species (H1 amplifier), exposing a new single-stranded region that opens a hairpin of the other species (H2 amplifier). This process, in turn, exposes a single-stranded region identical to the original initiator. The resulting chain reaction leads to the formation of a nicked double helix that grows until the hairpin supply is exhausted.

isHCR in the present invention combines binder-biomolecule interaction with hybridization Chain Reaction (HCR), wherein the binder may be an antibody or a genetically-engineered protein tag for labeling a target biomolecule.

Click chemistry is a class of biocompatible reactions intended primarily to join substrates of choice with specific biomolecules. Click chemistry is not a single specific reaction, but describes a way of generating products that follow examples in nature, which also generates substances by joining small modular units. In general, click reactions usually join a biomolecule and a reporter molecule. Click chemistry is not limited to biological conditions: the concept of a "click" reaction has been used in pharmacological and various biomimetic applications. However, they have been made notably useful in the detection, localization and qualification of biomolecules.

Antibody in the present invention includes but not limited to traditional IgGs and nanobodies.

EXAMPLES

Methods and Materials

Reagents and reagent preparation. DNA oligos were synthesized by Thermo Fisher Scientific and Sangon Biotech. Detailed sequences and modifications of DNA oligos can be found in Table 1. All oligos were dissolved in ddH$_2$O and stored at −20° C. Benzylguanine (BG)-labeled oligos were prepared by first mixing NH$_2$-Oligo (2 mM, 4 µL), HEPES (200 mM, 8 µL; pH=8.5), and BG-Gal-NHS (20 mM in DMSO, 12 µL; 591515, NEB) for 30 min at room temperature, and then purified using Micro Bio-Spin P-6 Gel columns (7326221, Bio-Rad).

The detailed information for antibodies and fluorescent reagents is shown in Table 2. Dextran sulfate (D8906) were purchased from Sigma-Aldrich. Graphene Oxide (GO, XF020, particle size <500 nm, C/O ratio=1.6) was obtained from Nanjing XFNANO.

Plasmid construction and AAV packaging. The genes encoding SNAPf, SpyCatcher, and GFP nanobody (LaG-16-2) were synthesized according to original reports. 4×SNAPf sequence was assembled by fusing four SNAPf-encoding sequences with short peptide linkers using Gibson cloning. scFv-GCN4-HA-GB1 sequence was amplified from pHR-scFv-GCN4-sfGFP-GB1-NLS-dWPRE (Addgene plasmid #60906, a gift from Ron Vale). The amino acid sequence smFP_GCN4 was designed based on the originally-reported smFPs sequence (Table 3). For membrane targeting, a GAP43-palmitoylation sequence was added by PCR to the 5' end of GFP, SNAPf, and smFP_GCN4 (hereafter named mGFP, mSNAPf and msmFP_GCN4). Two tandem mitochondria targeting sequences from human Cox8a were amplified by PCR from genomic DNA of HeLa cells, and added to the 5' end of SNAPf by Gibson assembly (hereafter named mitoSNAP). H2B and human GBP1 sequence was amplified by PCR from genomic DNA of HeLa cells. A single SpyTag sequence was added to the 3' end of H2B by PCR (hereafter named H2B-SpyTag). mGFP, mitoSNAP, H2B-SpyTag, and msmFP_GCN4 were cloned into the pcDNA3.1 vector. scFv-GCN4-HA-GB1 and SpyCatcher were cloned into the pET-21a vector for bacterial cytosolic expression. LaG-16-2 was cloned into the pET-22b vector for bacterial periplasmic expression. AAV-DIO-mGFP was constructed as previously described. AAV-DIO-mSNAPf and AAV-DIO-4×SNAPf were constructed by inserting the sequences encoding mSNAPf or 4×SNAPf, in an inverted orientation, into an AAV-EF1a-DIO backbone derived from AAV-EF1α-DIO-hChR2(H134R)-mCherry (a gift from Karl Deisseroth). AAV vectors were packaged into the AAV2/9 serotype, with titers of 1-5×10$^{12}$ viral particles mL$^{-1}$.

Purification of recombinant protein. E. coli BL21 (DE3) cells harboring pET-21a-scFv-GCN4-HA-GB1 or pET-21a-SpyCatcher were grown in lysogeny broth (LB) medium supplemented with 100 µg mL$^{-1}$ ampicillin. Protein expression was induced with IPTG at a concentration of 0.1 M for 3 h at 37° C.

Cells were then pelleted by a 20-min spin at 2,000×g at 4° C. Cells were lysed via ultrasonic sonication. Cellular debris was removed via 1 h of centrifugation at 39,000×g at 4° C. The supernatant was bound to His-Select nickel affinity resin, washed with His-wash buffer (20 mM NaH$_2$PO$_4$, pH 8.0, 1 M NaCl, 20 mM imidazole), eluted with His-elution buffer (20 mM sodium phosphate, pH 8.0, 0.5 M NaCl, 250 mM imidazole), and the eluate was then dialyzed with phosphate buffer saline (PBS).

LaG-16-2 was expressed and purified according to the original report. In brief, E. coli BL21 (DE3) cells harboring pET-22b-LaG-16-2 were grown in LB medium supplemented with 100 µg mL$^{-1}$ ampicillin. Protein expression was induced with IPTG at a concentration of 0.1 M for 20 h at 12° C. Cells were pelleted via a 10-min of centrifugation at 5,000×g at 4° C. The periplasmic fraction was isolated by osmotic shock. This fraction was then bound to His-Select nickel affinity resin and purified as described above.

Protein-HCR DNA Initiator conjugation. The conjugation was performed using Maleimide-PEG2-NHS (SMCC, 746223, Sigma-Aldrich) or NHS-Azide (synthesized or purchased from Thermo Fisher Scientific, 26130) as linkers. For Maleimide-PEG2-NHS conjugation, proteins (IgGs, scFv, LaG-16-2 and SpyCatcher) were dialyzed into phosphate buffered saline (PBS, pH 7.4) and reacted with Maleimide-PEG2-NHS (7.5-fold molar excess) at room temperature for 2 h. Excess crosslinkers were removed from maleimide-activated proteins using Zeba spin columns (7000 MWCO). In parallel, thiol-modified HCR initiators were reduced using dithiothreitol (DTT, 100 mM) in PBS (1 mM EDTA, pH 8.0) for 2 h at room temperature, and then purified using Micro Bio-Spin P-6 Gel columns. The maleimide-activated proteins and reduced initiators (15-fold molar excess for IgGs; 7.5-fold for scFv, LaG-16-2; 3-fold for SpyCatcher) were mixed and reacted at room temperature for 2 h. HCR initiator-labeled proteins were purified using Amicon Ultra Centrifugal Filters (50 kDa MWCO) or Zeba spin columns (7000 MWCO).

For NHS-Azide conjugation, proteins were dialyzed into phosphate buffered saline (PBS, pH 7.4) and reacted with NHS-Azide (7.5-fold molar excess) at room temperature for 2 h. Excess crosslinkers were removed from azide-activated proteins using Zeba spin columns (7000 MWCO). The azide-activated proteins were mixed with DBCO-labeled HCR initiators (15-fold molar excess for IgGs; 7.5-fold for scFv, LaG-16-2; 3-fold for SpyCatcher) and then reacted at room temperature for 12 h. HCR initiator-labeled proteins were purified using Amicon Ultra Centrifugal Filters (50 kDa MWCO) or Zeba spin columns (7000 MWCO).

Cell culture and bacterial infections. HEK293T cells (ATCC CRL-3216) and HeLa cells (ATCC CCL-2) were used for the cultured-cell staining experiments. Cells were seeded on 12 mm #1.5 coverglass slips. Transfection was done using PEI. Cells were fixed with paraformaldehyde before subsequent experiments. The S. *Typhimurium* infection was performed according to a previous report.

Mice and virus injection. Animal care and use were in accordance with the institutional guidelines of the National Institute of Biological Sciences, Beijing (NIBS), as well as the governmental regulations of China.

Adult (8-12 weeks old) SERT-Cre mice [strain name: B6·Cg-Tg(S1c6a4-Cre)ET33Gsat; MMRRC; Davis, CA, USA], CaMKIIa-Cre [strain name: B6·Cg-Tg(Camk2a-cre) T29-1Stl/J], ChAT-Cre [strain name: B6; 12956-Chattm2 (cre)Lowl/J], and C57BL/6N mice of either sex were used. Mice were maintained with a 12/12 photoperiod (light on at 8 AM) and were provided food and water ad libitum. Mice were anaesthetized with pentobarbital (i.p., 80 mg×kg$^{-1}$) before surgery, and then placed in a mouse stereotaxic instrument. For each mouse, 350 nL of virus (AAV-DIO-mGFP, AAV-DIO-mSNAPf, or AAV-DIO-4×SNAPf) was infused into the target areas of mice via a glass pipette at rate of 50 nL·min$^{-1}$. All subsequent experiments were performed at least 3 weeks after virus injection to allow sufficient time for transgene expression.

Tissue sample preparation. Mice were anesthetized with an overdose of pentobarbital and perfused intracardially with PBS, followed by paraformaldehyde (PFA, 4% wt/vol in PBS). Tissues were dissected out and postfixed in 4% PFA for 4 h at room temperature or 1 d at 4° C. Tissue samples were first dehydrated in 30% sucrose solution for preparing thin sections (50 µm). Thin sections were prepared on a Cryostat microtome (Leica CM1950).

Immunohistochemistry. The detailed information, working concentrations, and incubation times for antibodies can be found in Table 2. For brain sections and cultured cells, samples were permeabilized with 0.3% Triton X-100 in PBS (PBST) and blocked in 2% BSA in PBST at room temperature for 1 h. Sections were then incubated with primary antibodies. Samples were washed three times in PBST and were then incubated with biotinylated or HCR initiator-conjugated secondary antibodies. For control experiments, we used a mixture containing equal amounts of fluorophore-conjugated secondary antibodies and biotinylated secondary antibodies. Samples were then washed again three times in PBST. The biotinylated secondary antibodies were visualized by fluorophore-conjugated Streptavidin or DNA-fluorophore HCR amplifiers. HCR initiator-conjugated secondary antibodies were visualized by DNA-fluorophore HCR amplifiers.

Labeling of isHCR initiators. All reagents were dissolved in HCR amplification buffer [5×sodium chloride citrate (SCC buffer), 0.1% vol/vol Tween-20, and 10% wt/vol dextran sulfate in ddH$_2$O]. After labeling with biotinylated secondary antibodies, samples were incubated in 1 µg·mL$^{-1}$ streptavidin at room temperature for 30 min. After being washed three times in PBST, samples were incubated with 0.5 µM DNA-biotin HCR initiators at room temperature for 30 min. Samples were then washed three times and stored in PBST.

For multiplexed amplification using multiple biotinylated secondary antibodies (FIG. 1a), the immunosignals of target proteins were amplified using isHCR sequentially. That is, after being labeled with two primary antibodies, samples were incubated with one of two biotinylated secondary antibodies against a primary antibody; the basic isHCR amplification protocol was then used to amplify the signal of the secondary antibody. Next, before the application of the second of the two biotinylated secondary antibodies, brain sections were incubated with streptavidin (0.5 µg·mL$^{-1}$, 30 min at room temperature) to block any unbound biotin units remaining on the first secondary antibody; biotin (5 ng·mL$^{-1}$, 30 min at room temperature) was then added to saturate the biotin binding sites of the streptavidin. Having blocked the reactivity of the first biotinylated secondary antibody, the second biotinylated secondary antibody was added and then amplified. For multiplexed labeling using HCR initiator-conjugated secondary antibodies (FIGS. 2c, 2d), the snap-cooled DNA-fluorophore HCR amplifiers are applied directly to initiator-labeled samples and then amplified with the basic isHCR amplification protocol (i.e., lacking any streptavidin step).

The labeling of genetically encoded tags (SNAP-tag, SpyTag, GFP, and smFP_GCN4) with HCR initiators was conducted as follows (FIG. 2e and FIG. 1b-1d). After membrane permeabilization, cultured-cell or brain-section samples were incubated with appropriate binding partners. For SNAP-tag labeling, we applied 0.1 µM BG-labeled HCR initiators or 0.5-1 µM SNAP-Surface Alexa Fluor 546 and incubated these samples at room temperature for 1 h. For SpyTag labeling, we applied 25 µM HCR initiator-labeled SpyCatcher and incubated these samples at room temperature for 2 h. For mGFP-labeled samples, we applied 1 µg·mL$^{-1}$ HCR initiator-labeled LaG-16-2 and incubated these samples overnight at 4° C. For smFP_GCN4 labeling, we applied 5 µg·m$^{-1}$ HCR initiator-labeled scFv-GCN4-HA-GB1 and incubated these samples at room temperature for 1 h. PBS was used as incubation buffer for SNAP-Surface Alexa Fluor 546. HCR amplification buffer was used for all HCR initiator-containing reagents. Samples were then washed three times with PBST, and stored in PBST.

isHCR amplification. Note that while the experimental steps regarding the isHCR initiators varied according the conjugation strategies, the basic isHCR amplification process is common to all of the experiments. First, HCR amplification buffer was prepared [5×sodium chloride citrate (SCC buffer), 0.1% vol/vol Tween-20, and 10% wt/vol dextran sulfate in ddH$_2$O]. Next, a pair of DNA-fluorophore HCR amplifiers were snap-cooled separately in 5×SSC buffer by heating at 95° C. for 90 s and cooling to room temperature over 30 min. Both of these amplifiers were then added to amplification buffer (typically to a final concentration of 12.5 nM for thin sections, or 150 nM for large volume samples). isHCR amplification proceeded as samples were incubated with this buffer overnight at room temperature, and free amplifiers were then removed by washing the three times with PBST prior to signal detection. Note that an additional graphene oxide step was added to this basic process for applications that demands background suppression. Briefly, to include the quenching step, GO (20 µg·mL$^{-1}$) was mixed with the amplifiers in amplification buffer. The amplifier/GO mixture was vortexed thoroughly and incubated at room temperature for at least 5 min before being added to initiator-labeled samples.

To perform multi-round amplification, we used DNA-biotin HCR amplifiers. Before use, DNA-biotin HCR amplifiers were snap-cooled. Samples were incubated with 12.5 nM DNA-biotin HCR amplifiers overnight at room temperature. After extensive washing, streptavidin (1 µg·mL$^{-1}$) was applied again to start the next round of amplification. The procedure of adding DNA-biotin HCR amplifiers and then streptavidin was repeated two or three times to achieve desired signal intensity. DNA-fluorophore amplifiers (12.5 nM) were used in the final round to visualize the signals. For control experiments, biotin and Alexa Fluor-488 dual-labeled HCR amplifiers were used for the first round of amplification. Alexa Fluor-546-labeled HCR amplifiers were used for the second round of amplification.

Fluorescence microscopy. Confocal microscopy was performed on a Zeiss Meta LSM510 confocal scanning microscope using a 10×0.3 NA, a 20×0.5 NA, a 63×1.4 NA, or a 100×1.3 NA objective, or on a Zeiss LSM880 confocal scanning microscope using a 20×0.5 NA or a 40×0.75 NA objective. Images were processed and measured with FIJI and Matlab.

To image the entire brain sections, we performed widefield fluoresce imaging using the Olympus VS120 virtual microscopy slide scanning system with a 10× objective. For slide scanner imaging, brain sections from both groups on the same slide were imaged during the same imaging run using identical light intensity and exposure time. The images were acquired at 16 bit and were converted directly to the TIFF format for publication.

Statistical significance was determined using t-test or Kolmogorov-Smirnov test. P<0.05 was considered significant.

TABLE 1

| Oligo nucleotide sequences and modifications | | |
|---|---|---|
| Name | Sequence (5' to 3') | Modifications |
| B1 I2 | ATATAgCATTCTTTCTTgAggAgggCAg CAAACgggAAgAg (SEQ ID NO: 1) | 5' Biotin |
| B1 I2 Amine | ATATAgCATTCTTTCTTgAggAgggCAg CAAACgggAAgAg (SEQ ID NO: 1) | 5' Amine |
| B1 I2 Thiol | ATATAgCATTCTTTCTTgAggAgggCAg CAAACgggAAgAg (SEQ ID NO: 1) | 5' Thiol |
| B1 I2 DBCO | ATATAgCATTCTTTCTTgAggAgggCAg CAAACgggAAgAg (SEQ ID NO: 1) | 5' DBCO |
| B1 Amplifier H1 546 | CgTAAAggAAgACTCTTCCCgTTTgCTg CCCTCCTCgCATTCTTTCTTgAggAggg CAgCAAACgggAAgAg (SEQ ID NO: 2) | 5' Alexa Fluor 546 |
| B1 Amplifier H2 546 | gAggAgggCAgCAAACgggAAgAgTCTT CCTTTACgCTCTTCCCgTTTgCTgCCCT CCTCAAgAAAgAATgC (SEQ ID NO: 3) | 3' Alexa Fluor 546 |
| B1 Amplifier H1 Terminal Biotin | CgTAAAggAAgACTCTTCCCgTTTgCTg CCCTCCTCgCATTCTTTCTTgAggAggg CAgCAAACgggAAgAg (SEQ ID NO: 2) | 5' Biotin |
| B1 Amplifier H2 Terminal Biotin | gAggAgggCAgCAAACgggAAgAgTCTT CCTTTACgCTCTTCCCgTTTgCTgCCCT CCTCAAgAAAgAATgC (SEQ ID NO: 3) | 3' Biotin |
| B1 Amplifier H1 Internal Biotin | CgTAAAggAAgACTCTTCCCgTTTgCTg CCCTCCTCgCATTCTTTCTTgAggAggg CAgCAAACgggAAgAg (SEQ ID NO: 2) | Internal Biotin |
| B1 Amplifier H2 Internal Biotin | gAggAgggCAgCAAACgggAAgAgTCTT CCTTTACgCTCTTCCCgTTTgCTgCCCT CCTCAAgAAAgAATgC (SEQ ID NO: 3) | Internal Biotin |
| B1 Amplifier H1 Internal Biotin and 5'-488 | CgTAAAggAAgACTCTTCCCgTTTgCTg CCCTCCTCgCATTCTTTCTTgAggAggg CAgCAAACgggAAgAg (SEQ ID NO: 2) | Internal Biotin 5' Alexa Fluor 488 |
| B1 Amplifier H2 Internal Biotin and 3'-488 | gAggAgggCAgCAAACgggAAgAgTCTT CCTTTACgCTCTTCCCgTTTgCTgCCCT CCTCAAgAAAgAATgC (SEQ ID NO: 3) | Internal Biotin 3' Alexa Fluor 488 |
| B5 I2 | ATATACACTTCATATCACTCACTCCCAA TCTCTATCTACCC (SEQ ID NO: 4) | 5' Biotin |
| B5 I2 Thiol | ATATACACTTCATATCACTCACTCCCAA TCTCTATCTACCC (SEQ ID NO: 4) | 5' Thiol |

TABLE 1-continued

Oligo nucleotide sequences and modifications

| Name | Sequence (5' to 3') | Modifications |
|---|---|---|
| B5 I2 DBCO | ATATACACTTCATATCACTCACTCCCAA TCTCTATCTACCC (SEQ ID NO: 4) | 5' DBCO |
| B5 Amplifier H1 488 | ATTggATTTgTAgggTAgATAgAgATTg ggAgTgAgCACTTCATATCACTCACTCC CAATCTCTATCTACCC (SEQ ID NO: 5) | 5' Alexa Fluor 488 |
| B5 Amplifier H2 488 | CTCACTCCCAATCTCTATCTACCCTACA AATCCAATgggTAgATAgAgATTgggAg TgAgTgATATgAAgTg (SEQ ID NO: 6) | 3' Alexa Fluor 488 |
| B4 I2 Thiol | ATATACACATTTACAGACCTCAACCTAC CTCCAACTCTCAC (SEQ ID NO: 4) | 5' Thiol |
| B4 Amplifier H1 647 | gAAgCgAATATggTgAgAgTTggAggTA ggTTgAggCACATTTACAgACCTCAACC TACCTCCAACTCTCAC (SEQ ID NO: 7) | 5' Alexa Fluor 647 |
| B4 Amplifier H2 647 | CCTCAACCTACCTCCAACTCTCACCATA TTCgCTTCgTgAgAgTTggAggTAggTT gAggTCTgTAAATgTg (SEQ ID NO: 8) | 3' Alexa Fluor 647 |

TABLE 2

Antibodies

Primary antibodies:

| Epitope | Vendor | Cat. No. | Dilution | Incubation Time |
|---|---|---|---|---|
| Tyrosine Hydroxylase (TH) | Millipore | ab152 | 1:1000 | Overnight at 4° C. for brain sections |
| Choline acetyltransferase (ChAT) | Millipore | AB144P | 1:500 | Overnight at 4° C. for brain sections |
| DOPA decarboxylase (AADC) | Abcam | ab3905 | 1:500 | 24 h at 4° C. for brain sections |
| Neuronal nitric oxide synthase (nNOS) | Sigma | N7280 | 1:500 | Overnight at 4° C. for brain sections |
| Dopamine Transporter (DAT) | Millipore | MAB369 | 1:500 | Overnight at 4° C. for brain sections |
| hGBP1 | Santa Cruz | sc-53857 | 1:1000 | 1 h at RT for Western blot |
| GFP | Thermo Fisher Scientific | A10259 | 1:1000 | Overnight at 4° C. for brain sections; 1 h at RT for cultured cells and western blotting |
| Ki67 | eBioscience | 14-5698-80 | 1:1000 | 1 h at RT for cultured cells |
| Tom20 | Santa Cruz | sc-11415 | 1:1000 | 1 h at RT for cultured cells |
| HA | BioLegend | 901505 | 1:500 | 1 h at RT for Western blot |

Secondary antibodies:

| Secondary ab. | Vendor | Label | Cat. No. | Dilution | Incubation Time |
|---|---|---|---|---|---|
| Goat anti-rabbit | Abcam | Biotin | ab6720 | 1:1000 | 2 h at RT for brain sections |
| Donkey anti-goat | Jackson ImmunoResearch | Biotin | 705-065-147 | 1:1000 | 2 h at RT for brain sections |
| Donkey anti-mouse | Jackson ImmunoResearch | Biotin | 715-065-151 | 1:1000 | 1 h at RT for cultured cells |
| Goat anti-rabbit | Thermo Fisher scientific | DNA HCR initiators | 31212 | 5 μg · mL$^{-1}$ | 2 h at RT for brain sections; 1 h at RT for Western blot and cultured cells |

TABLE 2-continued

Antibodies

| Goat anti-rat | Thermo Fisher scientific | DNA HCR initiators | 31220 | 5 μg · mL$^{-1}$ | 2 h at RT for brain sections; 1 h at RT for Western blot and cultured cells |

Fluorescent reagents:

| Name | Vendor | Label | Cat. No. | Conc. | Incubation Time |
| --- | --- | --- | --- | --- | --- |
| SNAP-Surface Alexa Fluor 546 | NEB | Alexa Fluor 546 | S9132S | 500 μM, 1:500-1:1000 | 30 min at RT |

TABLE 3

The protein sequence of smFP_GCN4. A total of nine GCN4 tags are inserted into a superfolder GFP scaffold.

```
MEELLSKNYHLENEVARLKKGSGSGEELLSKNYHLENEVARLKKGS
GSGEELLSKNYHLENEVARLKKGSGSGSKGEELFTGVVPILVELDG
DVNGHKFSVRGEGEGDATNGKLTLKFICTTGKLPVPWPTLVTTLGG
GVQCFSRYPDHMKRHDFFKSAMPEGYVQERTISFKDDGTYKTRAEV
KFEGDTLVNRIELKGIDFKEDGNILGHKLEYNFNSHNVYITADKQK
NGIKANFKIRHNVEGSGSGEELLSKNYHLENEVARLKKGSGSGEEL
LSKNYHLENEVARLKKGSGSGEELLSKNYHLENEVARLKKGSGSGD
GSVQLADHYQQNTPIGDGPVLLPDNHYLSTQSVLSKDPNEKRDHMV
LLEFVTAAGITHGMDELYKGSGSGEELLSKNYHLENEVARLKKGSG
SGEELLSKNYHLENEVARLKKGSGSGEELLSKNYHLENEVARLKK
```
(SEQ ID NO: 9)

Example 1

Multiplexed Labeling Using isHCR.

FIG. 1. (a) shows images of the dorsal striatum in mouse brain sections double immunostained for TH (green) and choline acetyltransferase (ChAT, red). The signals of each antigen were visualized sequentially using corresponding biotinylated secondary antibodies and isHCR. (b) HCR initiators were conjugated to GFP-nanobodies (LaG-16-2) using SMCC as the linker. mGFP proteins were expressed in the orbitofrontal cortex neurons in CaMKII-Cre transgenic mice using adeno-associated virus (AAV) vectors. The GFP signals in the superior colliculus were amplified using HCR initiator-conjugated GFP-nanobody and isHCR-546. (c) Schematic of rapid labeling using genetically encoded protein tags. Functionalized HCR initiators bind directly to protein tags and initiate the amplification process. AAV vectors that bear the Cre-dependent double-floxed inverse (DIO) open reading frame cassette containing genes encoding the SNAPf tag were constructed and packaged into AAV particles. The AAV vectors were injected into Cre-transgenic mice to achieve cell-type specific expression. (d) Confocal images of HEK293T cells and mouse brain labeled by SNAP-tag. The upper panel shows cells transiently expressing the mSNAPf-tag. The middle panel shows the DRN from SERT-Cre mice injected with AAV-DIO-mSNAPf. The bottom panel shows the medial septum from SERT-Cre mice injected with AAV-DIO-4×SNAPf. The tag-positive cells were labeled with benzylguanine-conjugated Alexa Fluor 546 (BG-546) or isHCR-546. Scale bars, 50 μm (a), 200 μm (b), 100 μm (d).

Example 2

Simultaneous Detection of Multiple Targets Using isHCR.

Figure 2:
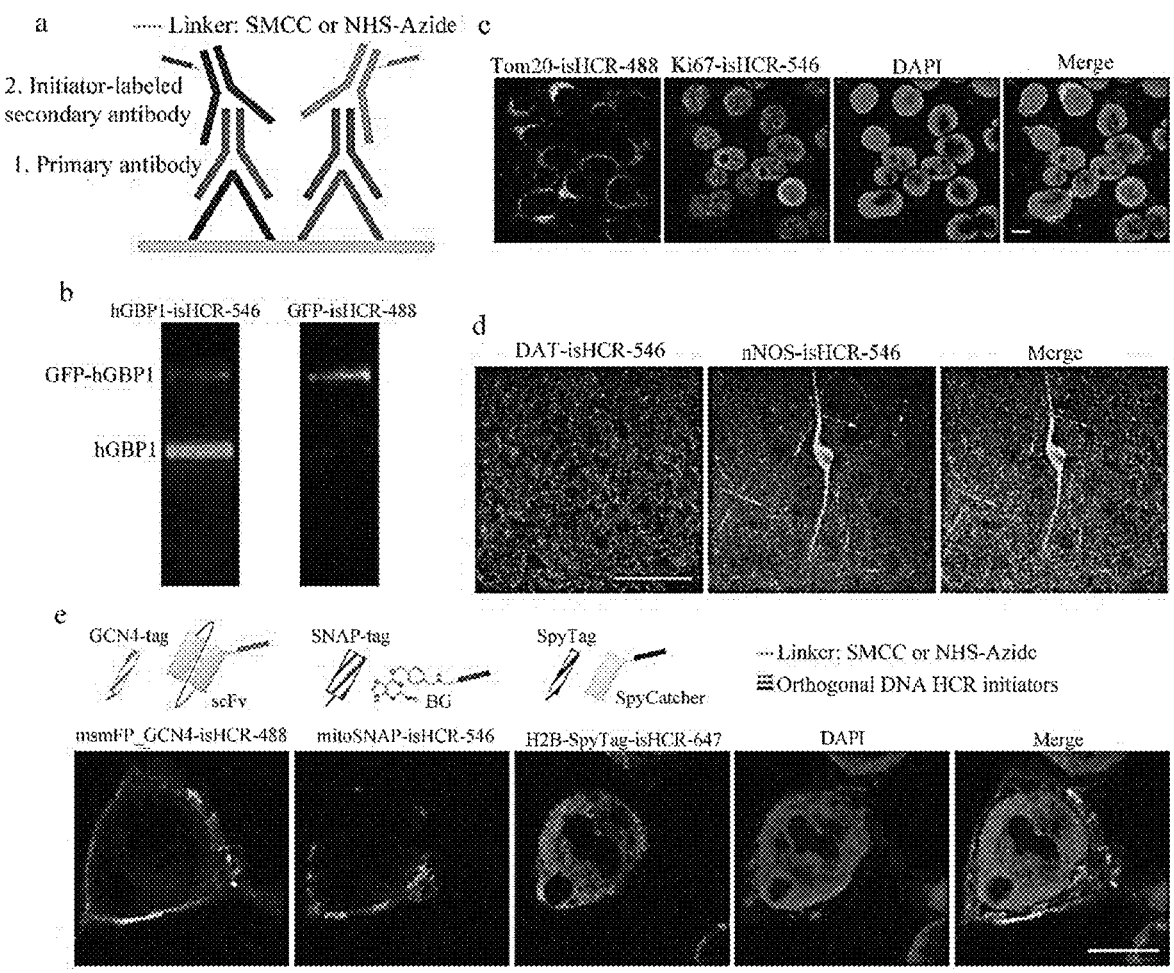
FIG. 2. Simultaneous detection of multiple targets using isHCR.

FIG. 2. (a) shows that two orthogonal HCR initiators can be conjugated directly onto secondary antibodies using either SMCC or Click Chemistry groups as linkers. (b) Western blot of a protein mixture containing purified hGBP1 and purified GFP-hGBP1 proteins. An anti-GFP primary antibody and an anti-hGBP1 primary antibody were applied. The two primary antibodies were detected using two secondary antibodies that were conjugated with different HCR initiators. (c) Images of HEK 293T cells immunostained against the nuclear protein Ki67 (red) and a mitochondria protein Tom20 (green) using two HCR initiator-conjugated secondary antibodies. The signals were then simultaneously amplified using isHCR-546 for Ki67 and isHCR-488 for Tom20. (d) Images of the dorsal striatum in mouse brain sections double immunostained against dopamine transporter (DAT, red) and neuronal nitric oxide synthase (nNOS, green) using two HCR initiator-conjugated secondary antibodies. The signals were then amplified simultaneously using isHCR-546 for DAT and isHCR-488 for nNOS. (e) Images of HEK 293T cells expressing three orthogonal protein tags targeting different cellular locations. The signals were simultaneously amplified using isHCR-488 for msmFP_GCN4, isHCR-546 for mitoSNAP, and isHCR-647 for H2B-SpyTag. Scale bar, 10 μm (c, e), 50 μm (d).

The invention claimed is:

1. A kit for detecting multiple target biomolecules, which comprises:
   (1) orthogonal binders;
   (2) orthogonal Hybridization Chain Reaction (HCR) initiators; and
   (3) orthogonal pairs of HCR amplifiers, wherein each of HCR initiators has a region for hybridizing with a HCR amplifier, and a region for conjugating the orthogonal binders, and the orthogonal binders target multiple target biomolecules respectively to allow HCR amplification directed to multiple target biomolecules,
   wherein the orthogonal binders are orthogonal antibodies, orthogonal single-domain antibodies (sdAbs), or fragments thereof,
   wherein the orthogonal HCR initiators are directly conjugated to the orthogonal binders using click chemistry linkers which are selected from NHS-Azide linker, NHS-DBCO linker, maleimide-azide linker, and maleimide-DBCO linker, and
   wherein the orthogonal HCR initiators are conjugated to the orthogonal binders by reacting DBCO-labeled HCR initiators with Azide-activated binders, and
   wherein the HCR amplifiers or the orthogonal pairs of HCR amplifiers are internally modified with a chemical group or a fluorescent dye, and the modification with a chemical group allows initiating further rounds of amplification.

2. The kit of claim 1, wherein the orthogonal antibodies are a collection of IgGs, the orthogonal sdAbs are a collection of sdAbs, and the fragments are a collection of scFvs.

3. The kit of claim 1, wherein the chemical group is selected from biotin, digoxigenin, acrydite, amine, succinimidyl ester, thiol, azide, TCO, Tetrazine, Alkyne, or DBCO, and the fluorescent dye is selected from Cyanine dyes, coumarin dyes, fluorescein dyes, and rhodamine dyes.

4. The kit of claim 3, wherein the pair of amplifiers comprise modification at internal positions, which are accessible to streptavidins and which serve as anchors for each successive round of branching in multi-round isHCR.

5. The kit of claim 1, further comprising grapheme oxide (GO).

6. The kit of claim 5, wherein GO has a particle size of <500 nm.

* * * * *

SEQUENCE LISTING

```
Sequence total quantity: 9
SEQ ID NO: 1           moltype = DNA  length = 41
FEATURE                Location/Qualifiers
misc_feature           1..41
                       note = Description of Artificial Sequence:
                       Syntheticpolynucleotide
source                 1..41
                       mol_type = other DNA
                       organism = synthetic construct
SEQUENCE: 1
```

```
atatagcatt ctttcttgag gagggcagca aacgggaaga g                    41

SEQ ID NO: 2           moltype = DNA   length = 72
FEATURE                Location/Qualifiers
misc_feature           1..72
                       note = Description of Artificial Sequence:
                       Syntheticpolynucleotide
source                 1..72
                       mol_type = other DNA
                       organism = synthetic construct
SEQUENCE: 2
cgtaaaggaa gactcttccc gtttgctgcc ctcctcgcat tctttcttga ggagggcagc    60
aaacgggaag ag                                                       72

SEQ ID NO: 3           moltype = DNA   length = 72
FEATURE                Location/Qualifiers
misc_feature           1..72
                       note = Description of Artificial Sequence:
                       Syntheticpolynucleotide
source                 1..72
                       mol_type = other DNA
                       organism = synthetic construct
SEQUENCE: 3
gaggagggca gcaaacggga agagtcttcc tttacgctct cccgtttgc tgccctcctc     60
aagaaagaat gc                                                       72

SEQ ID NO: 4           moltype = DNA   length = 41
FEATURE                Location/Qualifiers
misc_feature           1..41
                       note = Description of Artificial Sequence:
                       Syntheticpolynucleotide
source                 1..41
                       mol_type = other DNA
                       organism = synthetic construct
SEQUENCE: 4
atatacactt catatcactc actcccaatc tctatctacc c                       41

SEQ ID NO: 5           moltype = DNA   length = 72
FEATURE                Location/Qualifiers
misc_feature           1..72
                       note = Description of Artificial Sequence:
                       Syntheticpolynucleotide
source                 1..72
                       mol_type = other DNA
                       organism = synthetic construct
SEQUENCE: 5
attggatttg tagggtagat agagattggg agtgagcact tcatatcact cactcccaat    60
ctctatctac cc                                                       72

SEQ ID NO: 6           moltype = DNA   length = 72
FEATURE                Location/Qualifiers
misc_feature           1..72
                       note = Description of Artificial Sequence:
                       Syntheticpolynucleotide
source                 1..72
                       mol_type = other DNA
                       organism = synthetic construct
SEQUENCE: 6
ctcactccca atctctatct accctacaaa tccaatgggt agatagagat tgggagtgag    60
tgatatgaag tg                                                       72

SEQ ID NO: 7           moltype = DNA   length = 72
FEATURE                Location/Qualifiers
misc_feature           1..72
                       note = Description of Artificial Sequence:
                       Syntheticpolynucleotide
source                 1..72
                       mol_type = other DNA
                       organism = synthetic construct
SEQUENCE: 7
gaagcgaata tggtgagagt tggaggtagg ttgaggcaca tttacagacc tcaacctacc    60
tccaactctc ac                                                       72

SEQ ID NO: 8           moltype = DNA   length = 72
FEATURE                Location/Qualifiers
misc_feature           1..72
                       note = Description of Artificial Sequence:
                       Syntheticpolynucleotide
source                 1..72
```

```
                        mol_type = other DNA
                        organism = synthetic construct
SEQUENCE: 8
cctcaaccta cctccaactc tcaccatatt cgcttcgtga gagttggagg taggttgagg    60
tctgtaaatg tg                                                        72

SEQ ID NO: 9            moltype = AA  length = 459
FEATURE                 Location/Qualifiers
REGION                  1..459
                        note = Description of Artificial Sequence:
                         Syntheticpolypeptide
source                  1..459
                        mol_type = protein
                        organism = synthetic construct
SEQUENCE: 9
MEELLSKNYH LENEVARLKK GSGSGEELLS KNYHLENEVA RLKKGSGSGE ELLSKNYHLE    60
NEVARLKKGS GSGSKGEELF TGVVPILVEL DGDVNGHKFS VRGEGEGDAT NGKLTLKFIC   120
TTGKLPVPWP TLVTTLGGGV QCFSRYPDHM KRHDFFKSAM PEGYVQERTI SFKDDGTYKT   180
RAEVKFEGDT LVNRIELKGI DFKEDGNILG HKLEYNFNSH NVYITADKQK NGIKANFKIR   240
HNVEGSGSGE ELLSKNYHLE NEVARLKKGS GSGEELLSKN YHLENEVARL KKGSGSGEEL   300
LSKNYHLENE VARLKKGSGS GDGSVQLADH YQQNTPIGDG PVLLPDNHYL STQSVLSKDP   360
NEKRDHMVLL EFVTAAGITH GMDELYKGSG SGEELLSKNY HLENEVARLK KGSGSGEELL   420
SKNYHLENEV ARLKKGSGSG EELLSKNYHL ENEVARLKK                          459
```